(12) United States Patent
Iwamoto et al.

(10) Patent No.: US 10,717,961 B2
(45) Date of Patent: Jul. 21, 2020

(54) CELL CULTURE SYSTEM AND CELL CULTURE METHOD

(71) Applicants: ASAHI KASEI KABUSHIKI KAISHA, Tokyo (JP); TOKYO WOMEN'S MEDICAL UNIVERSITY, Tokyo (JP)

(72) Inventors: Ushio Iwamoto, Tokyo (JP); Michi Sato, Tokyo (JP); Kanako Konishi, Tokyo (JP); Katsuhisa Matsuura, Tokyo (JP); Tatsuya Shimizu, Tokyo (JP); Teruo Okano, Tokyo (JP)

(73) Assignees: ASAHI KASEI KABUSHIKI KAISHA, Tokyo (JP); TOKYO WOMEN'S MEDICAL UNIVERSITY, Tokyo (JP)

( * ) Notice: Subject to any disclaimer, the term of this patent is extended or adjusted under 35 U.S.C. 154(b) by 800 days.

(21) Appl. No.: 14/395,927

(22) PCT Filed: Apr. 24, 2013

(86) PCT No.: PCT/JP2013/062090
§ 371 (c)(1),
(2) Date: Oct. 21, 2014

(87) PCT Pub. No.: WO2013/161885
PCT Pub. Date: Oct. 31, 2013

(65) Prior Publication Data
US 2015/0118745 A1    Apr. 30, 2015

(30) Foreign Application Priority Data

Apr. 27, 2012 (JP) ................................ 2012-104078

(51) Int. Cl.
C12M 1/34 (2006.01)
C12M 1/00 (2006.01)
(Continued)

(52) U.S. Cl.
CPC ............ *C12M 41/44* (2013.01); *C12M 25/02* (2013.01); *C12M 25/12* (2013.01); *C12M 27/02* (2013.01);
(Continued)

(58) Field of Classification Search
CPC ...... C12M 41/44; C12M 25/02; C12M 25/12; C12M 27/02; C12M 27/18; C12M 29/04; C12M 29/10; C12M 29/26
See application file for complete search history.

(56) References Cited

U.S. PATENT DOCUMENTS 3,418,208 A   12/1968   Coty
5,286,646 A   2/1994    Kearns et al.
(Continued)

FOREIGN PATENT DOCUMENTS

EP   0 224 800   6/1987
EP   0 270 905   6/1988
(Continued)

OTHER PUBLICATIONS

Search report from E.P.O for 13780624.6, dated Mar. 24, 2015.
(Continued)

*Primary Examiner* — William H. Beisner
*Assistant Examiner* — Danielle B Henkel
(74) *Attorney, Agent, or Firm* — Greenblum & Bernstein, P.L.C.

(57) ABSTRACT

A cell culture system having a cell culture vessel, a composition controlling fluid storage vessel, a culture fluid composition controlling means having an inlet and an outlet for a cell culture fluid, an inlet-connected fluid feeding circuit from the cell culture vessel to the inlet of the culture fluid composition controlling means, an outlet-connected fluid feeding circuit from the cell culture vessel to the outlet of the culture fluid composition controlling means, a means (Continued)

which perfuses the cell culture fluid from the inlet-connected fluid feeding circuit to the outlet-connected fluid feeding circuit through the culture fluid composition controlling means, and a means which controls the amount of fluid in the cell culture vessel, in which compositions of the cell culture fluid in the cell culture vessel and compositions of the composition controlling fluid in the composition controlling fluid storage vessel can be controlled in a continuous manner.

26 Claims, 9 Drawing Sheets

(51) Int. Cl.
  *C12M 1/06* (2006.01)
  *C12M 1/12* (2006.01)
(52) U.S. Cl.
  CPC ............ *C12M 27/18* (2013.01); *C12M 29/04* (2013.01); *C12M 29/10* (2013.01); *C12M 29/26* (2013.01)

(56) References Cited

U.S. PATENT DOCUMENTS

| 7,879,601 | B2 | 2/2011 | Smith et al. | |
|---|---|---|---|---|
| 2003/0036192 | A1* | 2/2003 | Singh | B01F 11/0017 435/297.2 |
| 2003/0054544 | A1* | 3/2003 | Gruenberg | C12M 25/10 435/289.1 |
| 2010/0159524 | A1* | 6/2010 | Smith | C12M 27/02 435/91.1 |
| 2012/0270286 | A1 | 10/2012 | Takeuchi et al. | |

FOREIGN PATENT DOCUMENTS

| JP | S62-130683 | 6/1987 |
|---|---|---|
| JP | S63-226279 | 9/1988 |
| JP | H07-40928 | 5/1995 |
| JP | 9-201189 | 8/1997 |
| JP | 2011-036146 | 2/2011 |
| WO | 2009/016078 | 2/2009 |
| WO | 2011/058983 | 5/2011 |

OTHER PUBLICATIONS

English language abstract of EP0270905, which is a family member of JP S63-226279.
Côme et al., "Improvement of Culture Conditions of Human Embryoid Bodies Using a Controlled Perfused and Dialyzed Bioreactor System", *Tissue Engineering*, vol. 14, No. 4, 2008, pp. 289-298.
Schroeder et al., "Differentiation and Lineage Selection of Mouse Embryonic Stem Cells in a Stirred Bench Scale Bioreactor With Automated Process Control", *Biotechnology and Bioengineering*, vol. 92, No. 7, 2005, pp. 920-933.
International Search Report for PCT/JP2013/062090 dated Aug. 6, 2013, along with an English language translation.
English translation of the International Preliminary Report on Patentability for PCT/JP2013/062090, dated Oct. 28, 2014.

* cited by examiner

CELL CULTURE SYSTEM AND CELL CULTURE METHOD

TECHNICAL FIELD

The present invention relates to a cell culture system and a cell culture method.

BACKGROUND ART

Recently, besides conventional medicinal drugs containing a synthesized chemical substance as a main composition, medicinal drugs originated from biological materials produced by biotechnology, namely, biologics, have been increasingly used. Of the biologics, particularly remarkable biologics are cell products such as antibodies. These biologics have extremely high effects but expensiveness is a problem. Furthermore, since biologics are produced from organisms, there is possibility that variation in quality or the like during a production step is higher than that of conventional medicinal drugs. Accordingly, it has been required to develop a system for producing a product at low cost by culturing a large amount of cells at a time, and a culture system which can improve quality of a product by keeping a culture environment stable and maintaining quality of cells.

Moreover, in recent years, practical use of regenerative medicine using cells for therapy has begun. In Japan, some commercially available products, which have been approved by the pharmaceutical law, are presently used for the skin and cartilage tissue. As a therapy presently used, cells are partly taken from a patient, proliferated, and then formed into a tissue and transplanted. In the future, it is expected that a desired cell is induced from a somatic stem cell and a pluripotent stem cell and used in practical therapy. In realizing such a therapy, extremely a large amount of cells are required for preparing a sufficient size of tissue to be transplanted to a patient. According to estimation, cells in the order of $10^9$ are required, for example, for the left ventricle of the heart. To prepare such a large amount of cultured cells by currently available techniques, a great deal of labor and cost is required.

In addition, most of the cell culture steps presently employed are manually operated. Because of this, operation mistake and a risk of e.g., bacterial contamination of a culture system cannot be completely avoided.

As mentioned above, it has been desired to realize an effective culture system for culturing cells with a further higher density at low cost in an automated way. As a culture system satisfying these requirements, various systems have been proposed including a system using semipermeable membrane based on dialysis principle, in which cells are cultured while cleansing a culture fluid in a continuous manner (for example, see Patent Literatures 1 and 2).

However, if cells are cultured in these systems, pressure difference between outside and inside semipermeable membrane and concentration gradient of compositions are produced by perfusion of a culture fluid, with the result that the solvent of a culture fluid moves across the membrane. If a culture is carried out for a long time, the amount of fluid in a vessel decreases or increases, making it difficult to control of fluid amount in a culture vessel. Accordingly, stable culturing is difficult. Furthermore, when a culture is performed in these systems, it is usually required to increase a perfusion rate as much as possible in order to reduce a compositional change of a culture fluid; however, if a perfusion rate is increased more and more, the aforementioned control of fluid amount becomes difficult. Moreover, increasing the scale of culture results in increasing the perfusion rate. The same problem is produced.

As another method, Non Patent Literature 1 discloses a method of connecting a dialysis means to a rotor-type cell culture vessel. However, in such a culture, a specific cell culture vessel is required, which differs from the vessels of cell-culture apparatuses generally and widely used, and it is difficult to scale up a culture.

CITATION LIST

Patent Literature

Patent Literature 1: Japanese Patent Laid-Open No. 63-226279
Patent Literature 2: Japanese Patent Publication No. 7-40928

Non Patent Literature

Non Patent Literature 1: Biotechnology and Bioengineering, 2005; 92(7): 920

SUMMARY OF INVENTION

Technical Problem

The present invention provides a cell culture system for solving the above problems. More specifically, an object of the present invention is to provide a system applicable to various culture forms of cells and enabling to simultaneously attain low cost, power saving and high-density culture.

Solution to Problem

The present inventors have conducted intensive studies with the view of solving the above problems. As a result, we found that a system applicable to various culture forms of cells and enabling to simultaneously attain low cost, power saving and high-density culture, and easily attain scale-up of a culture can be provided by a cell culture system, which is characterized in that a cell culture fluid (e.g., a liquid as illustrated in FIGS. 1-3 discussed below in greater detail) in a cell culture vessel and a composition controlling fluid in a composition controlling fluid storage vessel can be controlled in a continuous manner by way of a culture fluid composition controlling means; at the same time, the amount of culture fluid in the cell culture vessel can be controlled to be substantially constant. Based on the finding, the present invention was accomplished.

More specifically, an aspect of the present invention is a cell culture system comprising a cell culture vessel for culturing cells, a composition controlling fluid storage vessel, a culture fluid composition controlling means having an inlet and an outlet for a cell culture fluid and/or composition controlling fluid and comprising a semipermeable membrane, an inlet-connected fluid feeding circuit from the cell culture vessel and/or the composition controlling fluid storage vessel to an inlet of the culture fluid composition controlling means, an outlet-connected fluid feeding circuit from the cell culture vessel and/or the composition controlling fluid storage vessel to an outlet of the culture fluid composition controlling means, a means which perfuses the cell culture fluid and/or the composition controlling fluid from the inlet-connected fluid feeding circuit to the outlet-connected fluid feeding circuit through the culture fluid composition controlling means, and a means which controls the amount of fluid in the cell culture vessel, wherein compositions of the cell culture fluid in the cell culture vessel and compositions of the composition controlling fluid in the composition controlling fluid storage vessel can be controlled by the culture fluid composition controlling means in a continuous manner; and at the same time, the amount of cell culture fluid in the cell culture vessel can be controlled to be substantially constant.

For example, in the cell culture system, the culture fluid composition controlling means may be disposed in the composition controlling fluid storage vessel, the culture fluid composition controlling means may have an inlet and an outlet for the cell culture fluid, the inlet-connected fluid feeding circuit may be connected to the inlet of the culture fluid composition controlling means from the cell culture vessel, the outlet-connected fluid feeding circuit may be connected to the outlet of the culture fluid composition controlling means from the cell culture vessel, and the perfusion means may perfuse the cell culture fluid from the inlet-connected fluid feeding circuit to the outlet-connected fluid feeding circuit through the culture fluid composition controlling means.

Alternatively, in the cell culture system, the culture fluid composition controlling means may be disposed in the cell culture vessel, the culture fluid composition controlling means may have an inlet and an outlet for the composition controlling fluid, the inlet-connected fluid feeding circuit may be connected to the inlet of the culture fluid composition controlling means from the composition controlling fluid storage vessel, the outlet-connected fluid feeding circuit may be connected to the outlet of the culture fluid composition controlling means from the composition controlling fluid storage vessel, and the perfusion means may perfuse the composition controlling fluid from the inlet-connected fluid feeding circuit to the outlet-connected fluid feeding circuit through the culture fluid composition controlling means.

Further alternatively, in the cell culture system, the culture fluid composition controlling means may be disposed outside the composition controlling fluid storage vessel and the cell culture vessel, the inlet-connected fluid feeding circuit may include a first inlet-connected fluid feeding circuit from the cell culture vessel to a first inlet of the culture fluid composition controlling means and a second inlet-connected fluid feeding circuit from the composition controlling fluid storage vessel to a second inlet of the culture fluid composition controlling means, the outlet-connected fluid feeding circuit may include a first outlet-connected fluid feeding circuit from the cell culture vessel to a first outlet of the culture fluid composition controlling means and a second outlet-connected fluid feeding circuit from the composition controlling fluid storage vessel to a second outlet of the culture fluid composition controlling means, wherein the semipermeable membrane may constitute a space between the first inlet and the first outlet and a space between the second inlet and the second outlet, and the perfusion means may have a means which perfuses the cell culture fluid from the first inlet-connected fluid feeding circuit to the first outlet-connected fluid feeding circuit through the culture fluid composition controlling means and a means which perfuses the composition controlling fluid from the second inlet-connected fluid feeding circuit to the second outlet-connected fluid feeding circuit through the culture fluid composition controlling means.

The perfusion means may have a fluid-feeding means which feeds the cell culture fluid in the cell culture vessel and/or the composition controlling fluid in the composition controlling fluid storage vessel to the culture fluid composition controlling means, and a fluid-returning means which returns the cell culture fluid and/or the composition controlling fluid, which was fed to the culture fluid composition controlling means where unnecessary substances in the cell culture fluid are allowed to be in contact with useful substances in the composition controlling fluid, feed amount V1 of fluid per hour by the fluid-feeding means and return amount V2 of fluid per hour by the fluid-returning means may satisfy $0.9 \times V1 \leq V2 \leq 1.1 \times V1$, and the total amount of cell culture fluid containing the cells may change within the range of 10%.

The cell culture system may further comprise a filter which is disposed in the inlet-connected fluid feeding circuit or the first inlet-connected fluid feeding circuit and which substantially passes the cell culture fluid and does not pass cells or cell aggregates at the inner end of the cell culture vessel.

Furthermore, an aspect of the present invention is a method for culturing cells, comprising a) providing the above cell culture system, b) supplying cells and the cell culture fluid to the cell culture vessel and supplying the culture fluid composition controlling fluid to the composition controlling fluid storage vessel, and c) continuously perfusing the cell culture fluid and/or the composition controlling fluid, wherein feed amount V1 of fluid per hour by the fluid-feeding means and return amount V2 of fluid per hour by the fluid-returning means are controlled to satisfy $0.9 \times V1 \leq V2 \leq 1.1 \times V1$, and the total amount of cell culture fluid containing the cells is controlled to change within the range of 10%.

Another aspect of the present invention is a cell culture system comprising, a cell culture vessel to which at least cells and a cell culture fluid are to be placed and in which the cells are cultured, a composition controlling fluid storage vessel to which a composition controlling fluid containing useful substances are to be placed, a culture fluid composition controlling means in which the cell culture fluid and the composition controlling fluid are brought into contact with each other to exchange substances, a fluid-feeding means which feeds the cell culture fluid in the cell culture vessel and/or the composition controlling fluid in the composition controlling fluid storage vessel to the culture fluid composition controlling means, and a fluid-returning means which returns the cell culture fluid and/or the composition controlling fluid brought into contact with each other, wherein feed amount V1 of fluid per hour by the fluid-feeding means and return amount V2 of fluid per hour by the fluid-returning means satisfy $0.9 \times V1 \leq V2 \leq 1.1 \times V1$, and the total amount of cell culture fluid containing the cells of the cell culture fluid changes within the range of 10%.

Further alternatively, an aspect of the present invention is a method for culturing cells, comprising placing at least cells and a cell culture fluid to a cell culture vessel to culture the cells, feeding the cell culture fluid in the cell culture vessel and/or the composition controlling fluid in a composition controlling fluid storage vessel, bringing the cell culture fluid and the composition controlling fluid into contact with each other through membrane, and returning the cell culture fluid and/or the composition controlling fluid brought into contact with each other through the membrane, wherein feed amount V1 of fluid per hour in the fluid-feeding step and return amount V2 of fluid per hour in the fluid-returning step satisfy $0.9 \times V1 \leq V2 \leq 1.1 \times V1$, and the total amount of cell culture fluid containing the cells of the cell culture fluid changes within the range of 10%.

In the cell culture system and cell culture method as mentioned above, for example, the cells are mammalian cells, which are embryonic stem cells (ES cells), induced pluripotent stem cells (iPS cells), mesenchymal stem cells, hematopoietic stem cells and/or cells differentiated and induced from these cells.

Furthermore, in the cell culture system and cell culture method as mentioned above, for example, the cells are cells applicable to floating culture, adhesive cells, cells forming cell aggregates and/or cells capable of adhering to a particle carrier. The cells capable of adhering to a particle carrier are cultured by placing cells and a particle carrier in a cell culture vessel.

Advantageous Effects of Invention

According to the present invention, it is possible to provide the cell culture system applicable to various culture forms of cells and enabling to simultaneously attain low cost, power saving and high-density culture.

DESCRIPTION OF EMBODIMENTS

Embodiments of the present invention will be described below. In the descriptions of the following drawings, the same or similar structural portions are designated by the same or similar numerical symbols. However, the drawings are schematically drawn. Accordingly, specific dimensions or the like should be determined with the reference to the following description. Needless to say, the drawings may contain portions having mutually different dimensional relationship and ratio.

Figure 1:
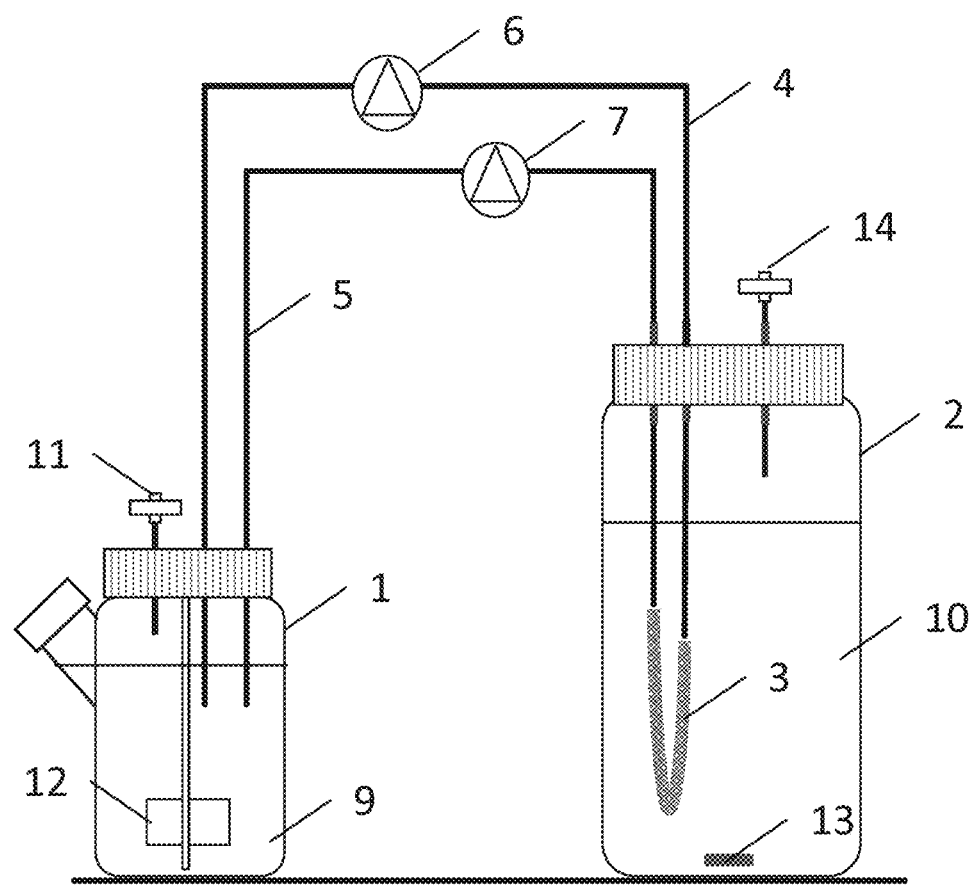
FIG. 1 is a schematic view showing an example of a cell culture system, in which a culture fluid composition controlling means is disposed in a composition controlling fluid vessel.

The cell culture system according to the embodiment comprises, as shown in FIG. 1, a cell culture vessel 1 for culturing cells, a composition controlling fluid storage vessel 2, a culture fluid composition controlling means 3 having an inlet and an outlet for a cell culture fluid 9 and/or a composition controlling fluid 10 and comprising semipermeable membrane, an inlet-connected fluid feeding circuit 5 from the cell culture vessel 1 and/or the composition controlling fluid storage vessel 2 to an inlet of the culture fluid composition controlling means 3, an outlet-connected fluid feeding circuit 4 from the cell culture vessel 1 and/or the composition controlling fluid storage vessel 2 to an outlet of the culture fluid composition controlling means 3, means 7 and 6 which perfuse the cell culture fluid 9 and/or the composition controlling fluid 10 from the inlet-connected fluid feeding circuit 5 to the outlet-connected fluid feeding circuit 4 through the culture fluid composition controlling means 3 and a means which controls the amount of fluid in the cell culture vessel 1. In the cell culture system, compositions of the cell culture fluid 9 in the cell culture vessel 1 and compositions of the composition controlling fluid 10 in the composition controlling fluid storage vessel 2 can be controlled in a continuous manner by way of the culture fluid composition controlling means 3; and at the same time, the amount of cell culture fluid 9 in the cell culture vessel 1 can be controlled to be substantially constant.

Figure 2:
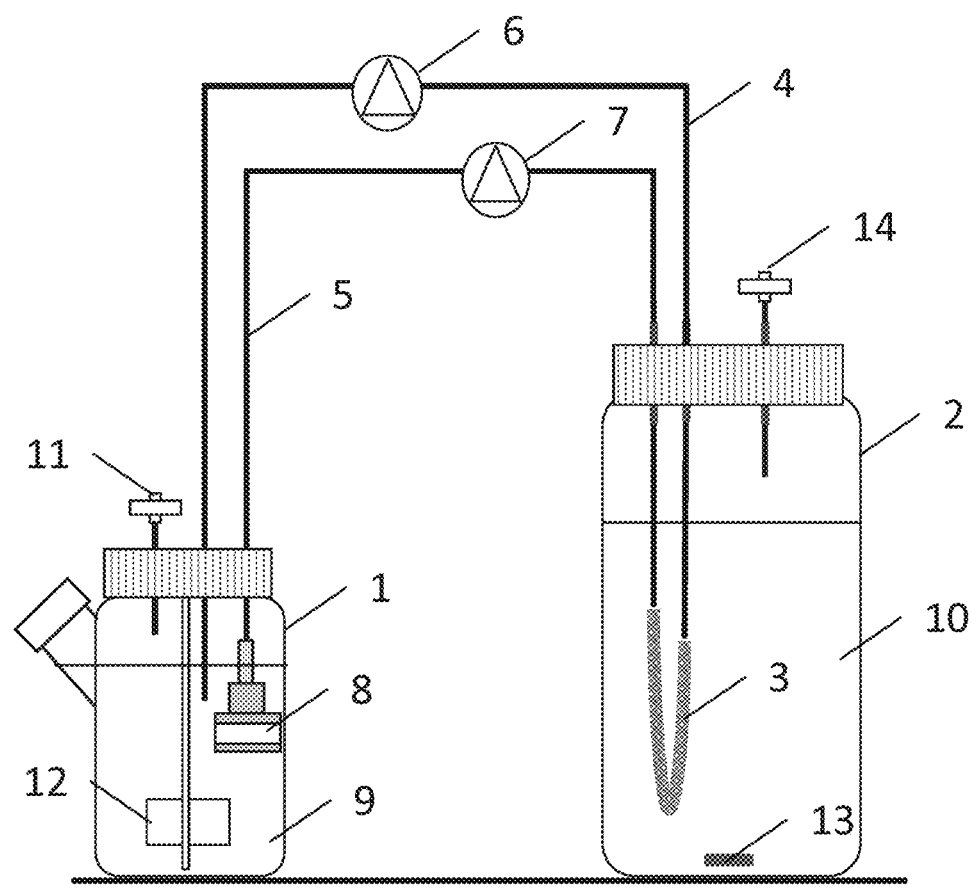
FIG. 2 is a schematic view showing an example of a cell culture system, in which a culture fluid composition controlling means is disposed in a composition controlling fluid vessel and a filter passing no cells is disposed in a cell culture vessel.

As shown in FIG. 2, in the cell culture vessel 1, a filter 8 may be attached to the end of the inlet-connected fluid feeding circuit 5 for preventing cells or cell aggregates from moving out of the cell culture vessel 1 together with the cell culture fluid 9. The filter 8 is not limited in material and shape as long as it has a structure by which cells or cell aggregates are rarely clogged on the surface of the filter; for example, a mesh or nonwoven cloth formed of stainless steel or nylon having an average pore diameter of 5 to 10 μm can be used for cells; whereas a flat-plate membrane formed of a polyethylene sintered compact or nonwoven cloth having an average pore diameter of 30 μm can be used for a cell aggregate. If the material of the filter has a property of easily adsorbing them, the material can be coated with another material or a surface modifier can be applied to suppress adsorption.

The cell culture fluid according to the embodiment refers to a solution at least containing fluid compositions and an environment required for growing cells among various types of cells. The compositions and concentrations are designed depending upon the features of the cells. Furthermore, the cell culture fluid is designed to have buffer capacity such that physiological pH is easily maintained and may contain a pH indicating pigment so as to easily determine pH change by color. Various types of cell culture fluids generally on the market each may be used as it is and these fluids, to which additional compositions are added depending upon the features of target cells, can be used.

The cells to be cultured in the culture system according to the embodiment are cells such as mammalian cells. As a result of culture, if a product (substance) from the cells is used, the cells easily producing the substance and cells to which a specific gene is introduced for the purpose of easily producing a desired substance, can be selected. Furthermore, as a result of cell culture, if specific cells are used, cells having a gene modified so as to facilitate proliferation of cells can be used, for example.

The degree of maturation of cells is not particularly limited. Not only matured cells but also undifferentiated cells may be used. For example, cells taken from a living tissue by an enzymatic treatment, cells derived from blood, mesenchymal stem cells, ES cells and iPS cells, are exemplified. Furthermore, the cells are not limited to adhesive cells or floating cells. Furthermore, the cells are not limited to single type of cells. Another type of cells producing a substance which facilitates growth of the desired cells may be mixed and cultured together.

The culture fluid composition controlling means according to the embodiment refers to semipermeable membrane through which a culture fluid composition permeates depending upon its molecular weight. The composition controlling fluid is brought into contact with a cell culture fluid through the culture fluid composition controlling means. The pore diameter of the culture fluid composition controlling means is designed depending upon the molecular weight of the composition desired to be kept in the cell culture vessel. More specifically, the pore diameter is selected such that a minimum molecular weight substance of the compositions that are desired to be kept in the cell culture vessel does not permeate the membrane. The shape of the culture fluid composition controlling means may be a flat membrane shape and a hollow fiber shape; however, for the purpose of perfusing a culture fluid and a composition controlling fluid, a hollow fiber shape is preferable.

Figure 3:
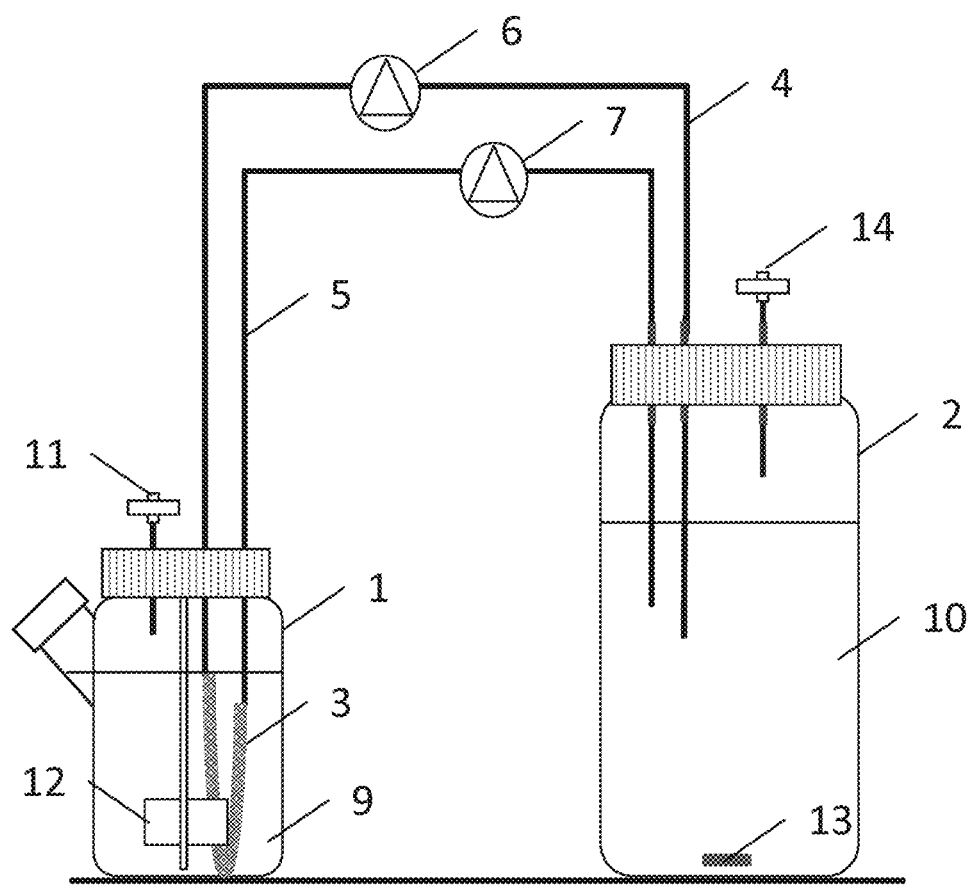
FIG. 3 is a schematic view showing an example of a cell culture system, in which a culture fluid composition controlling means is disposed in a cell culture vessel.

A material for the culture fluid composition controlling means is not particularly limited; however, a material which does not adsorb or decompose the compositions that are desired to be kept within the cell culture vessel is preferably used. Furthermore, if a material has a property of easily adsorbing such compositions, the material may be coated with another material and a surface modifier can be applied to suppress adsorption. The culture fluid composition controlling means 3 may be disposed in the cell culture vessel 1 as shown in FIG. 3, in the composition controlling fluid storage vessel 2 as shown in FIG. 1 and FIG. 2, or independently disposed outside the cell culture vessel 1 and the composition controlling fluid storage vessel 2 as shown in FIG. 4.

As described above, the cell culture system according to the embodiment may take at least three types of constitutions: 1) the culture fluid composition controlling means is disposed in the composition controlling fluid vessel, 2) the culture fluid composition controlling means is disposed in the cell culture vessel, and 3) the culture fluid composition controlling means is independently disposed outside the cell culture vessel and the composition controlling fluid storage vessel; however, the constitution can be selected depending upon the features of cells. For example, if the cells to be cultured are adhesive cells, constitutions 1) and 3) are preferably used in order to prevent deposition of cells onto the semipermeable membrane of the culture fluid composition controlling means disposed in the cell culture vessel. Furthermore, if the cells to be cultured are floating cells which grow while keeping a form of isolated cells, constitution 2) is preferably used.

Figure 4:
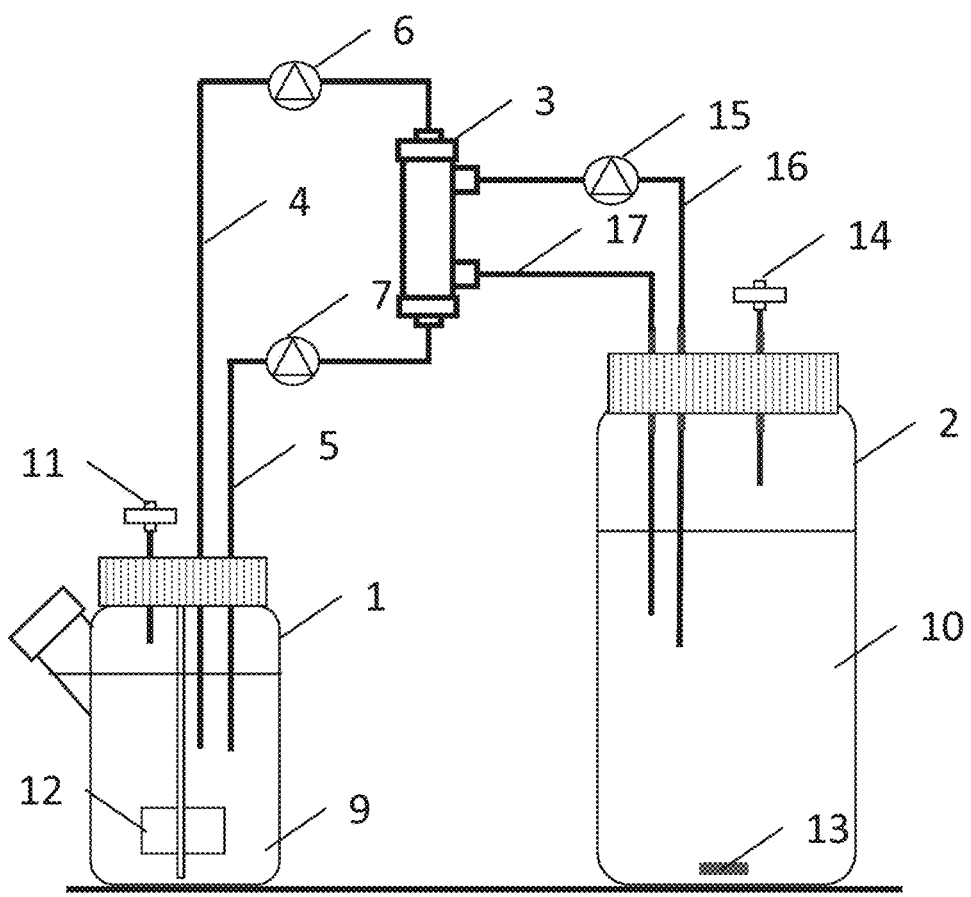
FIG. 4 is a schematic view showing an example of a cell culture system, in which a culture fluid composition controlling means is independently disposed outside a cell culture vessel and a composition controlling fluid storage vessel.

In the constitution shown in FIG. 4, the cell culture fluid 9 suctioned by the fluid-feeding means 7 from the cell culture vessel 1, passes through the first inlet-connected fluid feeding circuit 5, enters the hollow fiber module from the first inlet of the hollow fiber module, passes through the interior portion of the hollow fiber 3, further comes out from the first outlet of the hollow fiber module, passes through the first outlet-connected fluid feeding circuit 4 and returns to the cell culture vessel 1. The composition controlling fluid 10 suctioned by the fluid-feeding means 15 from the composition controlling fluid storage vessel 2 passes through the second inlet-connected fluid feeding circuit 17, enters the hollow fiber module from the second inlet of the hollow fiber module, passes though outside the hollow fiber 3, further comes out from the second outlet of the hollow fiber module, passes through the second outlet-connected fluid feeding circuit 16 and returns to the composition controlling fluid storage vessel 2.

The composition controlling fluid according to the embodiment refers to a solution containing at least one of the compositions substantially permeable though the culture fluid composition controlling means for cell culture fluid. The compositions contained in each of the culture fluid and the composition controlling fluid are controlled through the membrane based on the molecular weight and concentration difference between the two fluids.

A composition, which has a molecular weight larger than a pore diameter of the membrane and is substantially impermeable to the membrane, does not move between the two fluids. In contrast, a composition, which has the molecular weight smaller than a pore diameter of the membrane and is substantially permeable to the membrane, moves between the two fluids toward reducing its concentration difference. In this manner, the concentrations of the composition of the two liquids are controlled. A metabolite produced by cells and accumulated in the cell culture fluid moves to the composition controlling fluid side to lower its concentration in the culture fluid. Simultaneously, a composition required for growth of cells and reduced in concentration during a culture period moves from the composition controlling fluid to the culture fluid. In this manner, the culture fluid is supplemented with the composition. Based on the aforementioned principle, the environment of the culture fluid is maintained and satisfactory growth environment for cells is maintained by appropriately setting the content and concentration of the composition controlling fluid. Needless to say, the cell culture fluid can be used as it is. Accordingly, it is desirable that the composition controlling fluid have all compositions which will be consumed in the culture fluid during a cell culture period. It is further desirable that the concentrations of these compositions be set such that the compositions are not used up in a culture period.

The amount of composition controlling fluid is desirably set as large as possible in view of preventing accumulation of a cell metabolite. The amount of composition controlling fluid is desirably set five times or more and more desirably 10 times or more as large as the culture fluid. However, the amount of composition controlling fluid, since it influences culture cost, may be determined in consideration of a culture period and the number of requisite cells. Similarly to the cell culture fluid, the composition controlling fluid is designed to have a buffer capacity so as to easily maintain physiological pH and may contain a pH indicating pigment to easily determine a pH change by color, for example.

The cell culture vessel according to the embodiment is not limited in shape, size and material as long as the vessel is designed such that culture can be aseptically performed while keeping various types of cells and the culture fluid having fluid compositions required for growing the cells. Generally, these parameters are designed based on the properties of cells and the number of requisite cells. If the cells are adhesive cells, a vessel having a wide and planer structure is designed such that the cells precipitate by gravity and easily adhere to the surface. If the cells are floating cells, the vessel having a sufficiently deep structure is designed such that compositions of the culture fluid and oxygen concentration are easily homogenized by stirring with a rotary blade (stirring blade) 12 shown in FIG. 1 to FIG. 4.

Even in the case of adhesive cells, the adhesive cells can be cultured in a cell culture vessel designed for floating cells, if particle carriers are mixed. In this way, culture can be made while floating the particle carrier, to which the adhesive cells are allowed to adhere. Furthermore, adhesive cells, which are likely to associate with each other to form cell aggregates, can be cultured in a vessel designed for floating cells in accordance with floating culture.

As shown in FIG. 1 to FIG. 4, an aeration filter 11 may be disposed in the cell culture vessel 1.

In the cell culture vessel, a port for taking out the cell culture fluid and/or composition controlling fluid from the vessel and a port for returning fluid controlled in compositions to the vessel are each disposed.

The composition controlling fluid storage vessel according to the embodiment is not limited in shape, size and material as long as the vessel is designed such that the composition controlling fluid can be aseptically maintained during a culture period. Generally, these parameters are appropriately designed based on the amount of composition controlling fluid and whether or not the culture fluid composition controlling means is disposed in the vessel. In the composition controlling fluid storage vessel, a port for taking out the cell culture fluid and/or composition controlling fluid from the vessel and a port for returning fluid controlled in compositions to the vessel are each disposed.

As shown in FIG. 1 to FIG. 4, a stirring rotor 13 may be placed on the bottom surface of the composition controlling fluid storage vessel 2. Furthermore, an aeration filter 14 may be disposed to the composition controlling fluid storage vessel 2.

The fluid-feeding circuit according to the embodiment refers to a tube disposed among the cell culture vessel, composition controlling fluid storage vessel and culture fluid composition controlling means and having a tubular structure capable of aseptically perfusing a culture fluid or a composition controlling fluid. As the material, e.g., silicon, urethane, a fluorine resin and poly(vinyl chloride) are used.

The means which perfuses a cell culture fluid and/or a composition controlling fluid according to the embodiment refers to a means disposed so as to be in contact with the above fluid-feeding circuit and capable of continuously feeding the liquid within the circuit by application of power. A pump can be used as long as the pump is generally used and a Peri-Star pump and a diaphragm pump can be exemplified.

The means which controls the fluid amount of cell culture vessel according to the embodiment refers to a means which controls the volume of liquid in the cell culture vessel to be substantially constant during culture. The fluid-feeding means 7 and 6 shown in FIG. 1 to FIG. 4 may have such function. If semipermeable membrane formed of a hollow fiber is disposed in the culture apparatus and compositions are exchanged between the culture fluid and the composition controlling fluid through the semipermeable membrane and filtration pressure is applied to the membrane, consequently movement of both fluids occurs. Thus, unless a specific countermeasure is taken, the respective fluid amounts of culture fluid and composition controlling fluid sometimes change from the levels initially set. However, if the fluid amount of culture fluid changes, the concentrations of compositions and cell density in the culture fluid change, with the result that culture my not be stably performed. Then, if fluid-feeding means 7 and 6 such as a pump are independently disposed, for example, to the inlet and outlet of the semipermeable membrane, respectively, and independently controlled, the liquid volume can be maintained to be constant. As such a means, a method of controlling pressure of the air layers in the culture vessel and the composition controlling fluid storage vessel can be employed; however, a controlling method by at least two independent pumps as described above can be most simply and effectively performed.

In the embodiments shown in FIG. 1 and FIG. 2, for example, the fluid-feeding means 7 feeds the cell culture fluid 9 in the cell culture vessel 1 to the culture fluid composition controlling means 3. The fluid-feeding means 6 serves as a fluid-returning means which returns the cell culture fluid 9, which was fed to the culture fluid composition controlling means 3, in which the concentrations of unnecessary substances in the cell culture fluid 9 and the concentrations of useful substances in the composition controlling fluid 10 were controlled through the membrane.

In the embodiment shown in FIG. 3, for example, the fluid-feeding means 6 feeds the composition controlling fluid 10 in the composition controlling fluid storage vessel 2 to the culture fluid composition controlling means 3. The fluid-feeding means 7 serves as a fluid-returning means which returns the composition controlling fluid, which was fed to the culture fluid composition controlling means 3, in which unnecessary substances in the cell culture fluid 9 were allowed to be in contact with useful substances in the composition controlling fluid 10.

Herein, it is desirable that the feed amount V1 of fluid per hour by the fluid-feeding means and the return amount V2 of fluid per hour by the fluid-returning means ideally satisfy V1=V2; however, it is often difficult to realize completely equal amounts of fluids. Furthermore, the difference between V1 and V2 can be made to be extremely low; however, an extremely expensive and highly precise pump is often required. Nonetheless, if the amounts of fluids V1 and V2 fall within the range of $0.9 \times V1 \leq V2 \leq 1.1 \times V1$, the total amount of cell culture fluid can be easily controlled to change within the range of 10% by separately controlling V1 and V2, without a rapid change of fluid amount, which is thus preferable. Controlling the amounts of fluids V1 and V2 to fall within the above range can be easily attained by an inexpensive pump.

Figure 5:
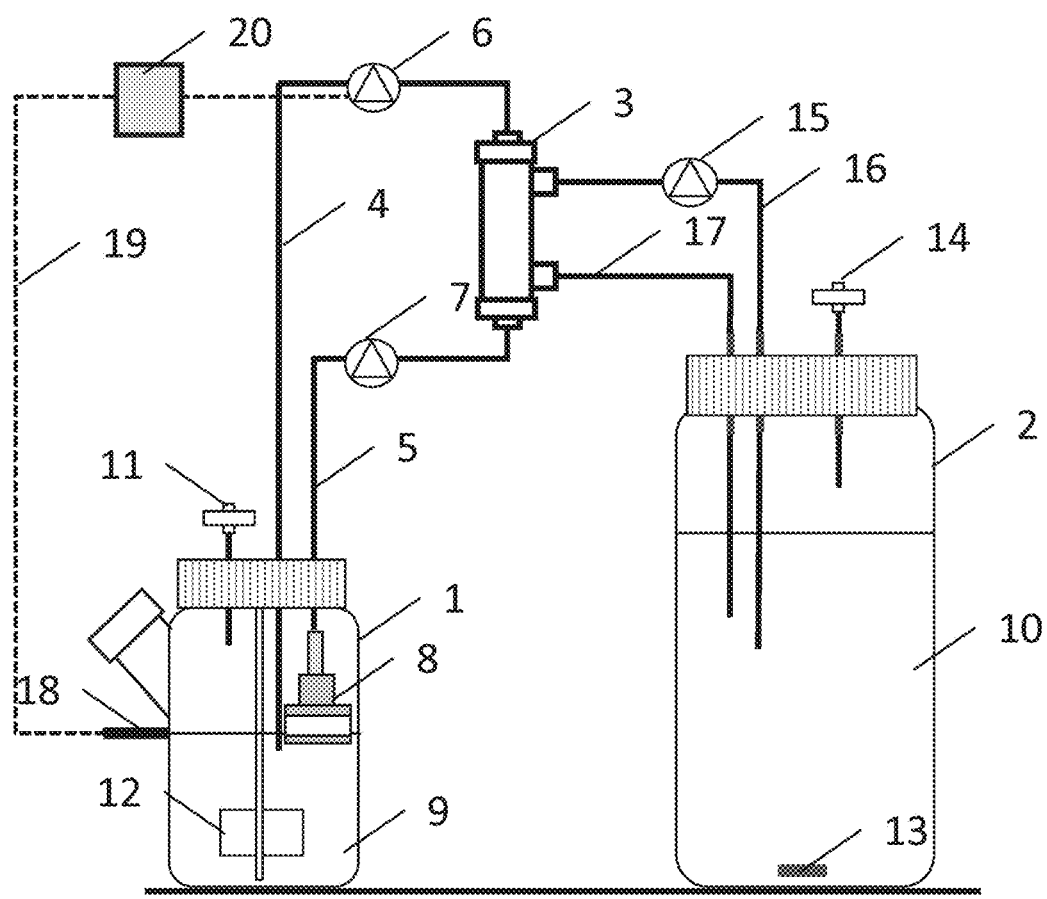
FIG. 5 is a schematic view showing an example of a cell culture system, in which a culture fluid composition controlling means is independently disposed outside a cell culture vessel and a composition controlling fluid storage vessel and a filter passing no cells is disposed in the cell culture vessel.

As described above, when at least two independent pumps are used, a system for controlling a fluid level can be constructed as shown in FIG. 5 as follows: information on whether the fluid level is higher or lower than a desired height is obtained by use of a means 18 which detects the fluid amount in the cell culture vessel 1 on an as-needed basis through a signal transduction circuit 19. Based on the information, a fluid-feeding means controller 20 such as a computer controls pumps 7 and 6 (which are connected to the inlet-connected fluid feeding circuit 5 and the outlet-connected fluid feeding circuit 4, respectively) to make a difference in flow rate. For example, even if the actual flow rate of each pump slightly differs from a preset value, accumulation of such a difference during long culture to produce a large difference in fluid level in the cell culture vessel can be prevented by such a control system.

Example 1

The present invention will be more specifically described below by way of Examples, which should not be construed as limiting the invention.

(Cell Culture System)

As a culture apparatus, 8-stage animal culture apparatus Bio Jr. 8 (BJR-25NA1S-8C, Able) was used. In the apparatus, 8 cell culture vessels (100 mL in each volume) can be controlled by a single controller. Measurement/control items are a stirring rate, temperature, pH and dissolved oxygen concentration (DO) and can be independently controlled in individual culture vessels.

(Preparation of ES Cells)

As the cells to be cultured, mouse ES cells (EMG7 strain) were selected.

(Culture of Embryoid Body)

(0th Day to 3rd Day after Initiation of Culture)

As a cell culture vessel, a specific vessel made of glass (Able) was used and 100 mL of culture fluid was used.

Culture was initiated by using mouse ES cells (density: $1 \times 10^5$ cells/mL). This time point was determined as 0th culture day.

As the culture fluid, Glasgow minimum essential medium (GMEM, Invitrogen) was used to which the following compositions were added.

More specifically, a culture fluid was prepared so as to contain a 10% fetal bovine serum (FBS, NICHIREI CORPORATION), 0.1 mM non-essential amino acid (NEAA, Invitrogen), 1 mM Na-pyruvate (Sigma) and 0.1 mM 2-mercaptoethanol (2-ME, Invitrogen).

Culture was continued up to the 3rd day as it was to form an aggregate of ES cells, i.e., an embryoid body (EB).

The cell culture vessel was equipped with a mixing rotary blade and the rotation number was set at 85 rpm.

The cell culture vessel was equipped with sensors capable of separately measuring temperature, pH and dissolved oxygen concentration.

Furthermore, the dissolved oxygen concentration was controlled to be 40%. For this, a gas introduction line was disposed to supply a gas mixture of oxygen, nitrogen and air to aerate the upper surface of the culture fluid in the cell culture vessel. Furthermore, a discharge line for discharging gas from the vessel was disposed.

(Third Day to Tenth Day after Initiation of Culture)

The total number of cells obtained on the 3rd culture day was calculated and the cells were cultured separately in accordance with the culture methods of Example 1 and Comparative Example. The cell density per culture vessel was set at $1.8 \times 10^5$ cells/mL.

In Example 1, a cell culture system as shown in FIG. 2 was prepared. More specifically, a cell culture vessel had a cover portion to which ports for taking out and returning a culture fluid were formed.

Furthermore, in the cell culture vessel, as a means which prevents cell aggregates from moving out together with a culture fluid outside the culture vessel, a flat-plate membrane formed of a polyethylene sintered compact and having a diameter of 15 mm and an average pore diameter of 30 μm was disposed.

As the composition controlling fluid vessel, a sterilized bottle (1 L in volume) made of glass was used.

To the cover portion of the vessel, an aeration line, an inlet line and an outlet line for the culture fluid were disposed.

As the culture fluid composition controlling means, a bundle of 400 hollow fibers available as Asahi polysulfone dialyzer APS (Asahi Kasei Kuraray Medical Co., Ltd.) having an effective length of 20 cm, was used by immobilizing it with urethane adhesive such that both ends of each of the hollow fibers having a tubular structure were opened.

The culture fluid composition controlling means was disposed within the composition controlling fluid storage means and both ends of the hollow-fiber bundle were connected to the inlet and outlet lines of a culture fluid, respectively in the form of a circuit.

As the composition controlling fluid, an FBS-free cell culture fluid (1 L) was used.

As the fluid-feeding circuit, a silicon tube (inner diameter: 1 mmφ, outer diameter: 4 mmφ) was used.

As a fluid-feeding means for a culture fluid, two Peri-Star pumps IPC-N4 (ISMATEC) were used. The two pumps were disposed separately in contact with the fluid-feeding circuits connecting the cell culture vessel and the composition controlling fluid storage vessel such that a fluid can be fed.

The cell culture system shown in FIG. 2 was prepared in accordance with the method described above.

An operation rate of the pumps was 100 mL/day from the 3rd day to the 4th day, 400 mL/day from the 4th day to the 5th day and 1,000 mL/day from the 5th day to the 10th day.

Culture was performed while continuously perfusing a culture fluid until the 10th day by fine-adjusting the flow rates of the two pumps such that the fluid volume in the cell culture vessel could be maintained at substantially the same level.

On the 10th day, cell culture was terminated and the number of cells was measured.

(Measurement of the Number of Cells)

On the 10th culture day, embryoid bodies were recovered from the cell culture vessel and treated with 0.25% trypsin/EDTA (Invitrogen) to obtain single cells. Thereafter, dead cells were stained with trypan blue dye and living cells alone were counted by use of a calculating board.

(Measurement of Lactic Acid Concentration)

A change of concentration of lactic acid in the culture fluid was obtained by taking a small amount of culture fluid from the cell culture vessel and measuring the concentration of lactic acid by a multifunctional biosensor BF-7 (Oji Scientific Instruments).

(Measurement of Equivalent Circular Diameter of EB)

The equivalent circular diameter of EB was obtained by photographing an EB image obtained by an optical microscope ECLIPSE Ti-U (Nikon Corporation), measuring the length of the outer periphery of EB by image analysis software (Nikon ElementsD, Nikon Corporation), calculating the resultant value assuming that the value represents the outer periphery length of a true circle. The equivalent circular diameters of 100 embryoid bodies per sample were obtained and a frequency distribution of equivalent circular diameters was prepared.

(TUNEL Staining of Inner Cells of EB)

TUNEL staining was performed in order to determine how much percentage of apoptotic cells is present in the inner cells of EB.

Frozen sections of EB were prepared from each sample and dead cells were stained by use of an apoptosis detection kit (Takara Bio Inc.).

Comparative Example 1

Culture was continued up to the 10th day by using an apparatus, which was used for culture up to the 3rd day.

Exchange of culture fluid was performed once in the period of the 4th to 5th day and twice in the period of the 6th to 9th day.

Exchange of the culture fluid was performed by terminating stirring in the cell culture vessel, allowing embryoid bodies to precipitate, and then removing the cell culture vessel from the apparatus, discarding the supernatant of the culture fluid in a clean bench and then adding a fresh culture fluid.

Exchange of a culture fluid was performed 10 times in total and 1 L of culture fluid in total was used.

Comparative Example 2

Culture was continued by using an apparatus prepared by removing the pump, which was attached to the fluid-feeding circuit for feeding a fluid from the composition controlling fluid storage vessel to the cell culture vessel, from the apparatus used in Example 1. As the culture proceeded, the amount of culture fluid in the cell culture vessel reduced. It became difficult to continue culture and culture was terminated.

(Results)

The total numbers of cells obtained on the 10th culture day in Example 1 and Comparative Example 1 are shown below.

Total number of cells in Example 1: $4.6 \times 10^8$

Total number of cells in Comparative Example 1: $3.4 \times 10^8$

Figure 6:
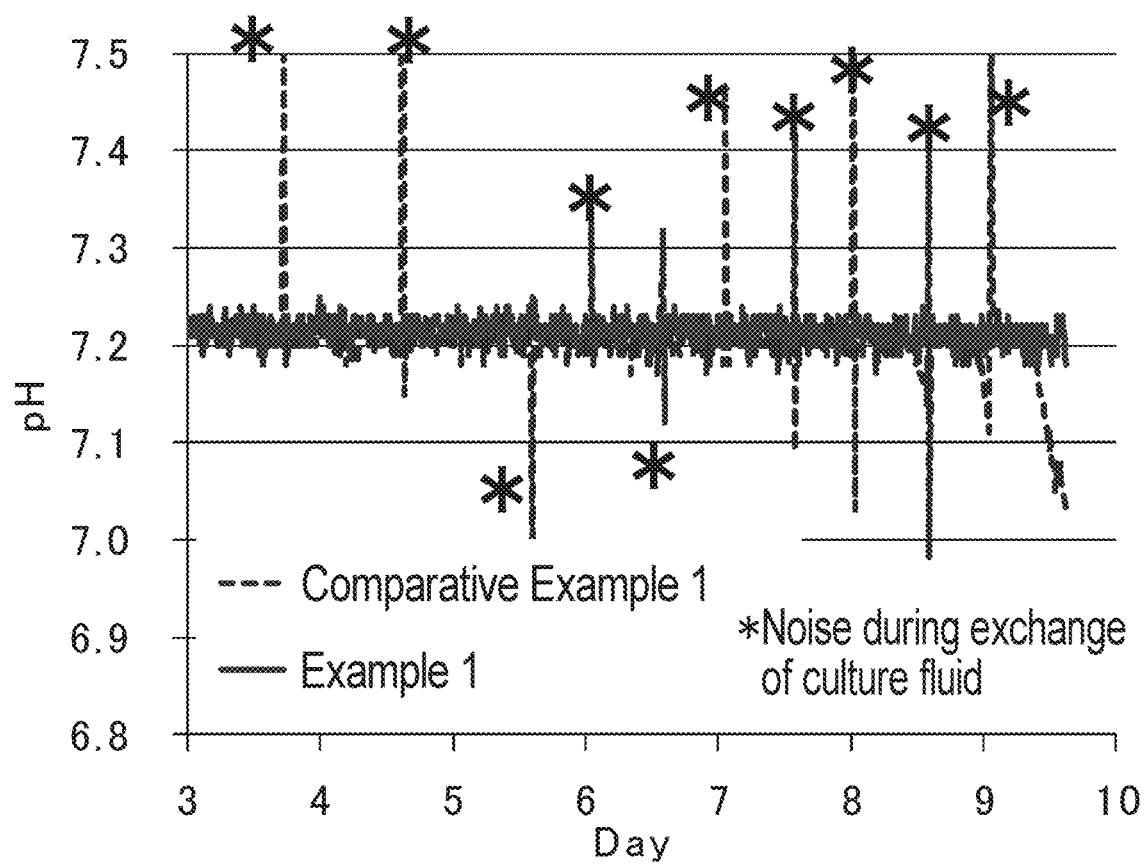
FIG. 6 is a graph showing a pH change of the cell culture fluid in a cell culture vessel.

A pH change of each of the cell culture vessels during 10-day culture period in Example 1 and Comparative Example 1 is shown in FIG. 6.

Figure 7:
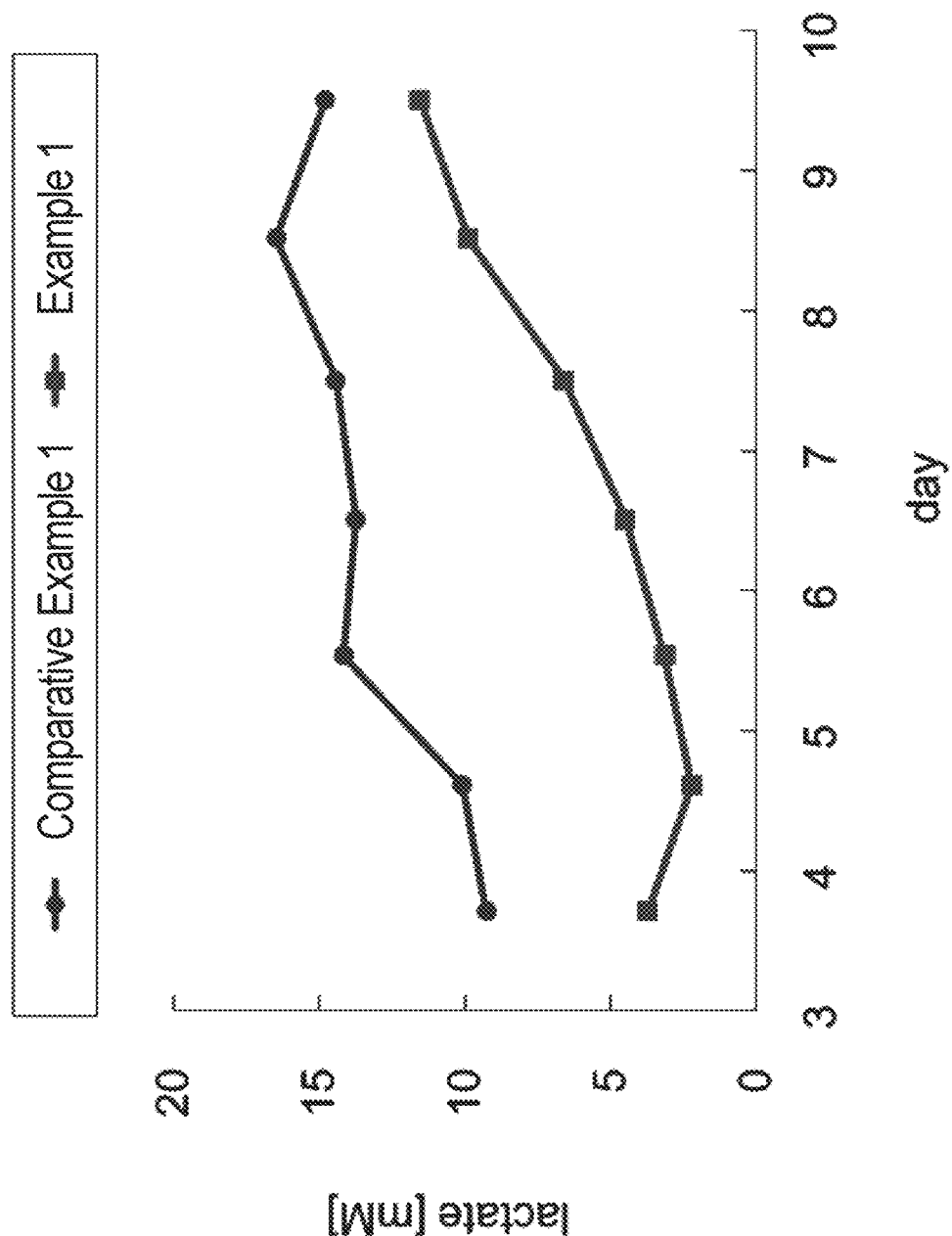
FIG. 7 is a graph showing a concentration change of lactic acid of the cell culture fluid in a cell culture vessel.

A lactic acid concentration change of each of the cell culture fluids in the cell culture vessels during the 10-day culture period in Example 1 and Comparative Example 1 is shown in FIG. 7.

Figure 8:
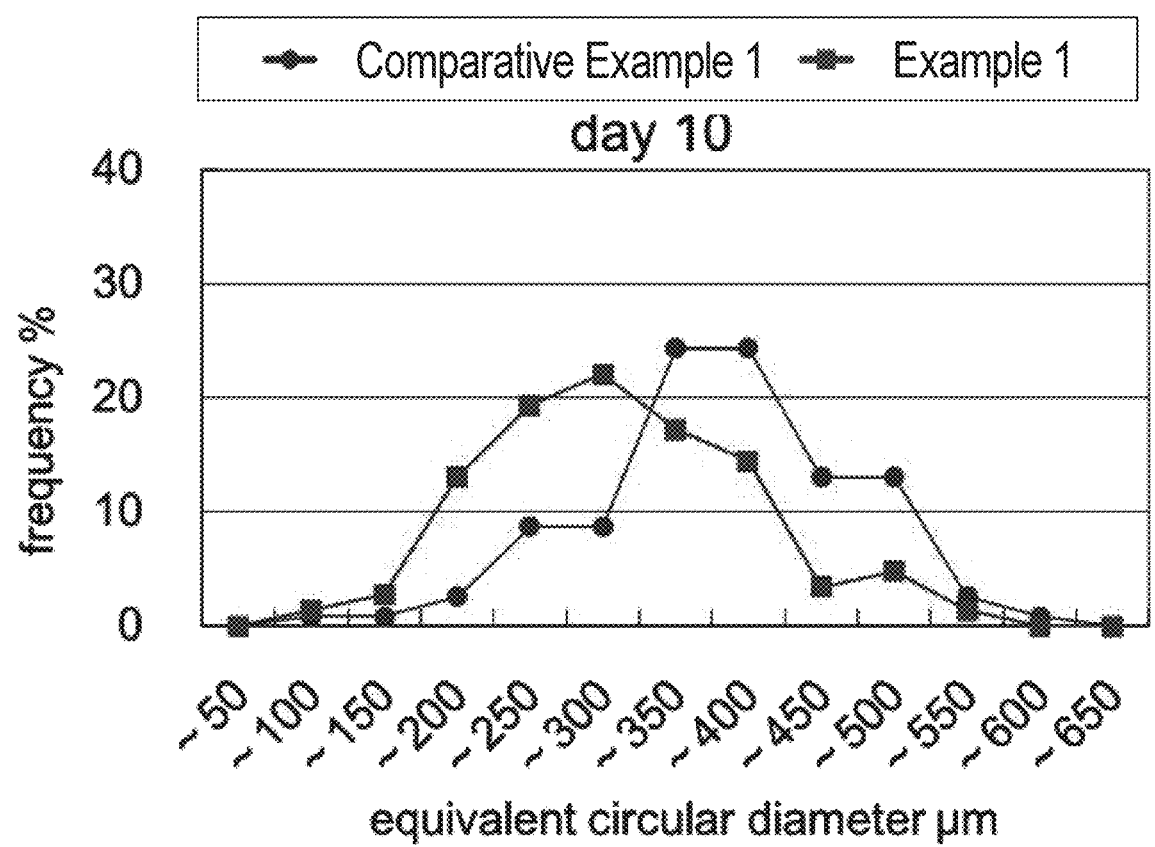
FIG. 8 is a graph showing an equivalent circular diameter distribution of an embryoid body (the 10th day of culture).

The equivalent circular diameters of the embryoid bodies obtained on the 10th culture day in each of Example 1 and Comparative Example 1 are shown in FIG. 8.

Figure 9:
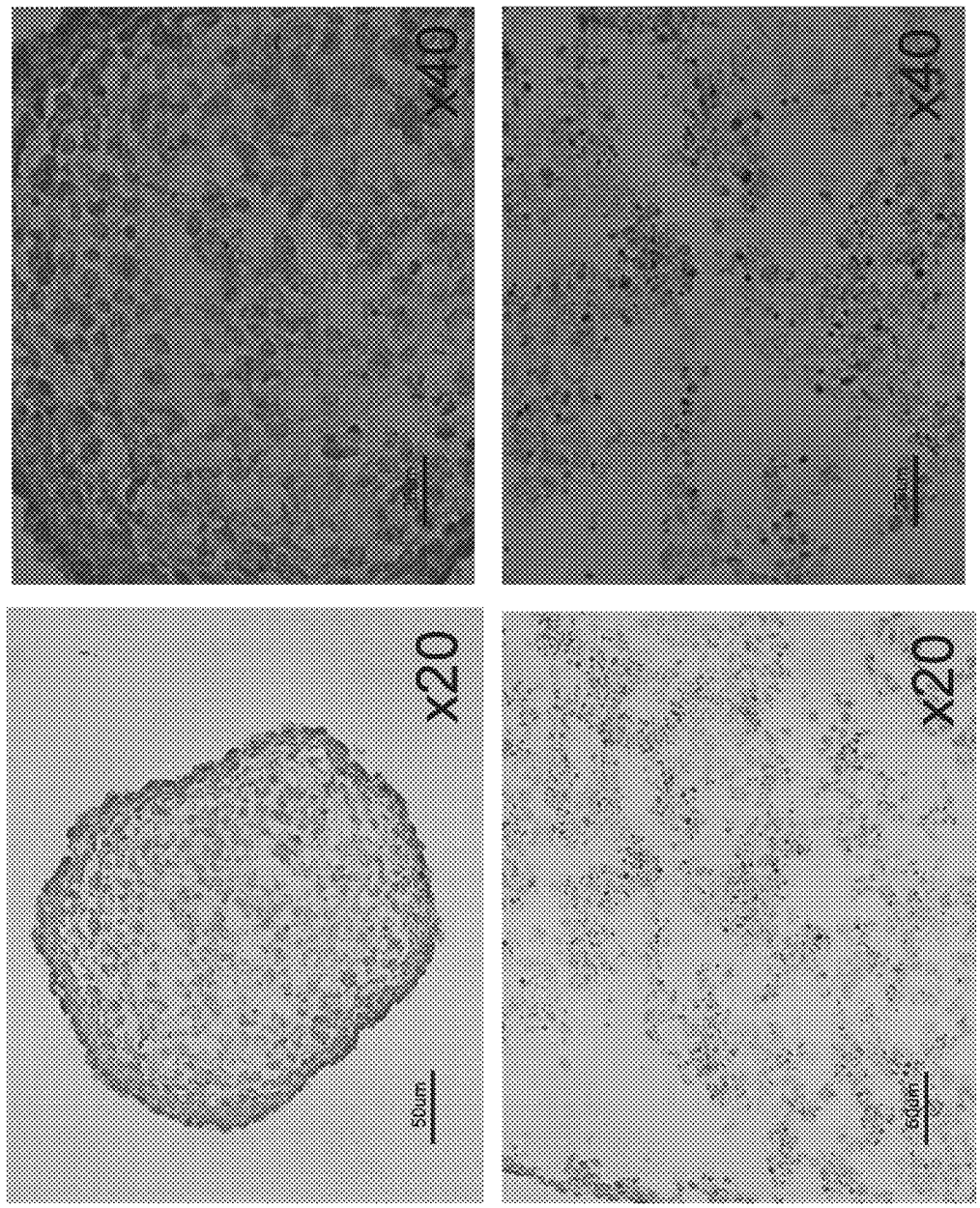
FIG. 9 is a graph showing a staining map of apoptosis cells in an embryoid body (the 10th day of culture).

The staining results of lyophilized slices of the embryoid bodies obtained on the 10th culture day in each of Example 1 and Comparative Example 1 are shown in FIG. 9. Apoptotic cells were stained in brown.

From the above results, in the cell culture system according to Example, exchange of a culture fluid is unnecessary and the amount of expensive serum used can be reduced to $\frac{1}{10}$; at the same time, the number of cells finally recovered was about 1.4 times. Because of such remarkable differences, the method of the present invention is demonstrated as an effective culture method. Furthermore, it was found that, in the culture method according to Example, accumulation of lactic acid is lower than that of Comparative Example and correspondingly pH is not reduced. In addition, it was confirmed that the diameter of EB at termination of culture is smaller than that of Comparative Example and the number of inner apoptotic cells tends to be low. Accordingly, it is considered that, in the cell culture system according to Example, a satisfactory culture environment can be maintained and suppression of apoptosis expression of inner cells of EB was attained.

Example 2

Preparation of ES Cells

Mouse ES cells (EMG7 strain) were selected as the cells to be cultured similarly to Example 1.

(Culture of Embryoid Body)

(0th day to 3rd day after initiation of culture) ES cells were cultured using four cell culture vessels in the same manner as in the 0th culture day to the 3rd culture day of Example 1.

(Third Day to Tenth Day after Initiation of Culture)

In Example 2, a cell culture system as shown in FIG. 5 was prepared. More specifically, the total number of cells obtained on the 3rd culture day from the four cell culture vessels was calculated. The cells were collected in a single large culture vessel (Able) made of glass so as to satisfy a cell density of $1.7 \times 10^5$ cells/mL and the volume of the culture fluid was adjusted to 1 L. The culture vessel was set in an animal cell culture apparatus BCP (BCP-03NP3S, Able) and culture was initiated.

As a culture fluid, the same culture fluid as in Example 1 was used.

In the cell culture vessel, a mixing rotary blade was disposed and the rotation number was set at 60 rpm.

The cell culture vessel was equipped with sensors capable of separately measuring temperature, pH and dissolved oxygen concentration.

Furthermore, the dissolved oxygen concentration was controlled to be 40%. For this, a gas introduction line was disposed for supplying a gas mixture of oxygen, nitrogen and air to aerate the upper surface of the culture fluid in the cell culture vessel. Furthermore, a discharge line for discharging gas from the vessel was disposed.

The cell culture vessel had a cover portion to which ports for taking out and returning a culture fluid were formed.

Furthermore, in the cell culture vessel, as a means which prevents cell aggregates from moving out together with a culture fluid outside the culture vessel, a flat-plate membrane formed of a polyethylene sintered compact and having a diameter of 47 mm and an average pore diameter of 30 μm was disposed on the upper surface of the fluid.

As the composition controlling fluid vessel, a polypropylene tank (10 L in volume) was used.

To a cover portion of the vessel, an aeration line, and an inlet line and an outlet line for a culture fluid were disposed.

As the culture fluid composition controlling means, a continuance-slow system blood filter, Excel Flow AEF-03 (Asahi Kasei Kuraray Medical Co., Ltd.) was used.

The culture fluid composition controlling means was independently disposed outside the cell culture vessel and the composition controlling fluid storage vessel.

The inlet line for a culture fluid was connected such that the culture fluid taken out from the cell culture vessel through the flat-plate membrane flowed through the interior portion of the hollow fiber in the form of a circuit. Next, the outlet line was connected such that the culture fluid passed through the interior portion of the hollow fiber returned to the culture vessel in the form of a circuit.

Subsequently, the inlet line and the outlet line were connected such that the composition controlling fluid is taken from the composition controlling fluid storage vessel, passed through the outside of the hollow fiber serving as the culture fluid composition controlling means and returned to the composition controlling fluid storage vessel.

As the composition controlling fluid, a serum-free cell culture fluid (10 L) was used.

As the fluid-feeding circuit, a freon tube (inner diameter: 2 raw, outer diameter: 4 mmφ) was used.

As the fluid-feeding means of a culture fluid, three Peri-Star pumps IPC-N4 (ISMATEC) were used. The three pumps were disposed separately in contact with fluid-feeding circuits connecting between the cell culture vessel and the culture fluid composition controlling means, and between the culture fluid composition controlling means and the composition controlling fluid storage vessel such that a fluid can be fed.

The cell culture vessel was further equipped with a fluid level detection means, i.e., a laser detector (KEYENCE CORPORATION). A controller programmed to stop operation of a Peri-Star pump if the fluid level increased, was disposed between this and the fluid-feeding pump of the outlet circuit 1.

The cell culture system shown in FIG. 5 was prepared in accordance with the method described above.

The operation rates of the pumps were as follows. From the 3rd day to the 4th day, the pump on inlet line 1 was set at 1 L/day and the pump of outlet line pump 1 was set at 1.1 L/day; from the 4th day to the 5th day, the pump on inlet line 1 was set at 4 L/day and the outlet line pump 1 was set at 4.4

L/day; and from the 5th day to the 10th day, the pump on inlet line 1 was set at 10 L/day, and the pump on the outlet line 1 was set at 11 L/day. The operation rate of the pump for feeding a composition controlling fluid was set at a value 4 times as high as that of the pump on the inlet line 1.

Culture was performed while continuously perfusing a culture fluid until the 10th day by fine-adjusting the flow rates of the pumps such that the fluid volume in the cell culture vessel could be maintained at substantially the same level by the system.

On the 10th day, cell culture was terminated and the number of cells was measured.

(Results)

The total number of cells obtained on the 10th culture day in Example and Comparative Example is shown below.

Total number of cells in Example 2: $5.7 \times 10^9$

From the above results, it was confirmed that scale-up of a culture can be easily attained by the cell culture system according to Example.

Example 3

Preparation of Cells

As the cells to be cultured, commercially available floating cells, i.e., CHO cells (derived from the ovary of a Chinese hamster, Life Technologies) were selected.

(0th Day to 7th Day after Initiation of Culture)

In Example 3, a cell culture system as shown in FIG. 3 was prepared. More specifically, as the cell culture vessel, a CULSTIR flask (double arm type, equipped with a stirrer, Sibata Scientific Technology Ltd.) was used and a culture fluid of 300 mL was used.

Culture was initiated by seeding the CHO cells at a density of $2 \times 10^5$ cells/mL. This time point was determined as the 0th culture day.

As the culture fluid, CD-CHO medium (Life Technologies) was used.

The cell culture vessel was equipped with a mixing rotary blade and the rotation number was set at 80 rpm.

The cell culture vessel had a cover portion to which ports for taking out and returning a culture fluid were formed.

As the composition controlling fluid vessel, a sterilized bottle (500 mL in volume) made of glass was used.

To a cover portion of the cell culture vessel, an aeration line, and an inlet line and an outlet line for the composition controlling fluid were disposed.

As the culture fluid composition controlling means, a bundle of 100 hollow fibers available as Asahi polysulfone dialyzer APS (Asahi Kasei Kuraray Medical Co., Ltd.) having an effective length of 25 cm, was used by immobilizing it with urethane adhesive such that both ends of each of the hollow fibers having a tubular structure were opened.

The culture fluid composition controlling means was disposed within the cell culture vessel and both ends of the hollow-fiber bundle were connected to the inlet and outlet lines for the composition controlling fluid, respectively in the form of a circuit.

As the composition controlling fluid, a CD-CHO medium (300 mL) was used.

As the fluid-feeding circuit, a silicon tube (inner diameter: 1 imp, outer diameter: 4 mmφ) was used.

The two vessels were placed in an incubator (IP400, Yamato Scientific Co., Ltd.) at 37° C. in a 5% $CO_2$ atmosphere.

As a fluid-feeding means for a composition controlling fluid, two Peri-Star pumps (SJ-121H, ATTO) were used. The two pumps were separately disposed in contact with fluid-feeding circuits connecting the cell culture vessel and the composition controlling fluid storage vessel such that a fluid can be fed.

The cell culture system shown in FIG. 3 was prepared in accordance with the method described above.

An initial operation rate of the pumps was 0.22 mL/minute from the 0th day to the 4th day; and 0.62 mL/minute from the 4th day to the 7th day.

Culture was performed while continuously perfusing a culture fluid until the 7th day by fine-adjusting the flow rates of the two pumps such that the fluid volume in the cell culture vessel could be maintained at substantially the same level.

Comparative Example 3

Using an apparatus only having the cell culture vessel of Example (the culture fluid composition controlling means was not used, either), culture was continuously performed up to the 7th day in the same manner as in Example.

(Results)

The densities of living cells obtained on the 7th culture day in Example 3 and Comparative Example 3 are shown below.

Density of cells in Example 3: $66.8 \times 10^5$ cells/mL

Density of cells in Comparative Example 3: $28.9 \times 10^5$ cells/mL

It was confirmed that the cell culture system according to Example is also effectively applied to floating cells which are proliferated while keeping a form of isolated cells, as described above.

INDUSTRIAL APPLICABILITY

The cell culture system and cell culture method according to the embodiments can be applied to various culture forms of mammalian cells and enable to simultaneously attain low cost, power saving and high-density culture. Accordingly, the present invention can be used in the field in which a large amount of product such as a protein is produced by cells and in the field in which a large amount of cells, themselves are cultured and used.

REFERENCE SIGNS LIST

1 Cell culture vessel
2 Composition controlling fluid storage vessel
3 Culture fluid composition controlling means
4 Fluid-feeding circuit
5 Fluid-feeding circuit
6 Fluid-feeding means
7 Fluid-feeding means
8 Filter
9 Cell culture fluid
10 Composition controlling fluid
11 Aeration filter
12 Stirring blade
13 Stirring rotor
14 Aeration filter
15 Fluid-feeding means
16 Fluid-feeding circuit
17 Fluid-feeding circuit
18 Fluid level detection means
19 Signal transduction circuit
20 Fluid-feeding means controller

The invention claimed is:

1. A cell culture system comprising:
a cell culture vessel for culturing cells;
a component controlling liquid storage vessel;
a culture liquid component controller having an inlet and an outlet for a cell culture liquid and comprising a semipermeable membrane;
an inlet-connected liquid feeding circuit from the cell culture vessel to an inlet of the culture liquid component controller;
an outlet-connected liquid feeding circuit from the cell culture vessel to an outlet of the culture liquid component controller;
a liquid-feeding pump and a liquid-returning pump configured to perfuse the cell culture liquid from the inlet-connected liquid feeding circuit to the outlet-connected liquid feeding circuit through the culture liquid component controller; and
wherein the liquid-feeding pump and the liquid-returning pump are configured to control the amount of liquid in the cell culture vessel,
wherein the liquid-feeding pump is disposed to the inlet-connected liquid feeding circuit and the liquid-returning pump is disposed to the outlet-connected liquid feeding circuit,
wherein the culture liquid component controller is configured to control components of the cell culture liquid in the cell culture vessel and components of the component controlling liquid in the component controlling liquid storage vessel in a continuous manner to reduce a difference between concentrations of the components of the cell culture liquid and concentrations of the components of the component controlling liquid; and at the same time, the liquid-feeding pump and the liquid-returning pump are independently controlled to control the amount of cell culture liquid in the cell culture vessel to be substantially constant,
wherein the culture liquid component controller is disposed in the component controlling liquid storage vessel,
wherein the culture liquid component controller has an inlet and an outlet for the cell culture liquid,
wherein the inlet-connected liquid feeding circuit is directly connected to the inlet of the culture liquid component controller from the cell culture vessel,
wherein the outlet-connected liquid feeding circuit is directly connected to the outlet of the culture liquid component controller from the cell culture vessel, and
wherein the liquid-feeding pump and the liquid-returning pump are configured to perfuse the cell culture liquid from the inlet-connected liquid feeding circuit to the outlet-connected liquid feeding circuit through the culture liquid component controller,
wherein the liquid-feeding pump is configured to feed the cell culture liquid in the cell culture vessel to the culture liquid component controller, and the liquid-returning pump is configured to return the cell culture liquid, which was fed to the culture liquid component controller where unnecessary substances in the cell culture liquid are allowed to be in contact with useful substances in the component controlling liquid,
wherein feed amount V1 of liquid per hour by the liquid-feeding pump and return amount V2 of liquid per hour by the liquid-returning pump satisfy $0.9 \times V1 \leq V2 \leq 1.1 \times V1$, and the total amount of cell culture liquid containing the cells changes within the range of 10%.

2. The cell culture system according to claim 1, further comprising a filter which is disposed in the inlet-connected liquid feeding circuit and is configured to pass the cell culture liquid and does not pass cells or cell aggregates at the inner end of the cell culture vessel.

3. A method for culturing cells, comprising:
a) providing the cell culture system according to claim 1;
b) supplying cells and the cell culture liquid to the cell culture vessel and supplying the culture liquid component controlling liquid to the component controlling liquid storage vessel, and;
c) continuously perfusing the cell culture liquid,
wherein feed amount V1 of liquid per hour by the liquid-feeding pump and return amount V2 of liquid per hour by the liquid-returning pump are controlled to satisfy $0.9 \times V1 \leq V2 \leq 1.1 \times V1$, and the total amount of cell culture liquid containing the cells is controlled to change within the range of 10%.

4. The cell culture system according to claim 1, wherein the cells are mammalian cells.

5. The cell culture system according to claim 4, wherein the mammalian cells are embryonic stem cells (ES cells), induced pluripotent stem cells (iPS cells), mesenchymal stem cells, hematopoietic stem cells and/or cells differentiated and induced from these cells.

6. The cell culture system according to claim 1, wherein the cells are cells applicable to floating culture, adhesive cells, cells forming cell aggregates and/or cells capable of adhering to a particle carrier.

7. The cell culture method according to claim 6, wherein the cells capable of adhering to a particle carrier are cultured by placing the cells and the particle carrier in a cell culture vessel.

8. The cell culture system according to claim 1, wherein the culture liquid component controller is formed of hollow fibers.

9. A cell culture system comprising:
a cell culture vessel for culturing cells;
a component controlling liquid storage vessel;
a culture liquid component controller having an inlet and an outlet for component controlling liquid and comprising a semipermeable membrane;
an inlet-connected liquid feeding circuit from the component controlling liquid storage vessel to an inlet of the culture liquid component controller;
an outlet-connected liquid feeding circuit from the component controlling liquid storage vessel to an outlet of the culture liquid component controller;
a liquid-feeding pump and a liquid-returning pump configured to perfuse the component controlling liquid from the inlet-connected liquid feeding circuit to the outlet-connected liquid feeding circuit through the culture liquid component controller,
wherein the liquid-feeding pump and the liquid-returning pump are configured to control the amount of liquid in the cell culture vessel,
wherein the liquid-feeding pump is disposed to the inlet-connected liquid feeding circuit and the liquid-returning pump is disposed to the outlet-connected liquid feeding circuit,
wherein the culture liquid component controller is configured to control components of the cell culture liquid in the cell culture vessel and components of the component controlling liquid in the component controlling liquid storage vessel in a continuous manner to reduce a difference between concentrations of the components of the cell culture liquid and concentrations of the components of the component controlling liquid; and at the same time, the liquid-feeding pump and the liquid-returning pump are independently controlled to control the amount of cell culture liquid in the cell culture vessel to be substantially constant, wherein the culture liquid component controller is disposed in the cell culture vessel, wherein the culture liquid component controller has an inlet and an outlet for the component controlling liquid, wherein the inlet-connected liquid feeding circuit is directly connected to the inlet of the culture-liquid component controller from the component controlling liquid storage vessel, wherein the outlet-connected liquid feeding circuit is directly connected to the outlet of the culture liquid component controller from the component controlling liquid storage vessel, wherein the liquid-feeding pump and the liquid-returning pump are configured to perfuse the component controlling liquid from the inlet-connected liquid feeding circuit to the outlet-connected liquid feeding circuit through the culture-liquid component controller, wherein the liquid-feeding pump is configured to feed the component controlling liquid in the component controlling liquid storage vessel to the culture liquid component controller, and the liquid-returning pump is configured to return the component controlling liquid, which was fed to the culture liquid component controller where unnecessary substances in the cell culture liquid are allowed to be in contact with useful substances in the component controlling liquid, and wherein feed amount V1 of liquid per hour by the liquid-feeding pump and return amount V2 of liquid per hour by the liquid-returning pump satisfy $0.9 \times V1 \leq V2 \leq 1.1 \times V1$, and the total amount of cell culture liquid containing the cells changes within the range of 10%.

10. The cell culture system according to claim 9, wherein the culture liquid component controller is formed of hollow fibers.

11. A method for culturing cells, comprising:
a) providing the cell culture system according to claim 9;
b) supplying cells and the cell culture liquid to the cell culture vessel and supplying the culture liquid component controlling liquid to the component controlling liquid storage vessel, and;
c) continuously perfusing the component controlling liquid, wherein feed amount V1 of liquid per hour by the liquid-feeding pump and return amount V2 of liquid per hour by the liquid-returning pump are controlled to satisfy $0.9 \times V1 \leq V2 \leq 1.1 \times V1$, and the total amount of cell culture liquid containing the cells is controlled to change within the range of 10%.

12. The cell culture system according to claim 9, wherein the cells are mammalian cells.

13. The cell culture system according to claim 12, wherein the mammalian cells are embryonic stem cells (ES cells), induced pluripotent stem cells (iPS cells), mesenchymal stem cells, hematopoietic stem cells and/or cells differentiated and induced from these cells.

14. The cell culture system according to claim 9, wherein the cells are cells applicable to floating culture, adhesive cells, cells forming cell aggregates and/or cells capable of adhering to a particle carrier.

15. The cell culture method according to claim 14, wherein the cells capable of adhering to a particle carrier are cultured by placing the cells and the particle carrier in a cell culture vessel.

16. A cell culture system comprising:
a cell culture vessel for culturing cells;
a component controlling liquid storage vessel;
a culture liquid component controller having an inlet and an outlet for a cell culture liquid and a component controlling liquid and comprising a semipermeable membrane;
an inlet-connected liquid feeding circuit from the cell culture vessel and the component controlling liquid storage vessel, the inlet-connected liquid feeding circuit directly connected to the inlet of the culture liquid component controller;
an outlet-connected liquid feeding circuit from the cell culture vessel and the component controlling liquid storage vessel, the outlet-connected liquid feeding circuit directly connected to the outlet of the culture liquid component controller; and
a liquid-feeding pump, a liquid-returning pump, and a component controlling liquid pump which are configured to perfuse the cell culture liquid and the component controlling liquid from the inlet-connected liquid feeding circuit to the outlet-connected liquid feeding circuit through the culture liquid component controller;
wherein the liquid-feeding pump and the liquid-returning pump are configured to control the amount of liquid in the cell culture vessel,
wherein the liquid-feeding pump is disposed to the inlet-connected liquid feeding circuit and the liquid-returning pump is disposed to the outlet-connected liquid feeding circuit,
wherein the culture liquid component controller is configured to control components of the cell culture liquid in the cell culture vessel and components of the component controlling liquid in the component controlling liquid storage vessel in a continuous manner to reduce a difference between concentrations of the components of the cell culture liquid and concentrations of the components of the component controlling liquid; and at the same time, the liquid-feeding pump and the liquid-returning pump are independently controlled to control the amount of cell culture liquid in the cell culture vessel to be substantially constant,
wherein the culture liquid component controller is disposed outside the component controlling liquid storage vessel and the cell culture vessel,
wherein the inlet-connected liquid feeding circuit includes a first inlet-connected liquid feeding circuit from the cell culture vessel to a first inlet of the culture liquid component controller and a second inlet-connected liquid feeding circuit from the component controlling liquid storage vessel to a second inlet of the culture liquid component controller,
wherein the outlet-connected liquid feeding circuit includes a first outlet-connected liquid feeding circuit from the cell culture vessel to a first outlet of the culture liquid component controller and a second outlet-connected liquid feeding circuit from the component controlling liquid storage vessel to a second outlet of the culture liquid component controller,
wherein the semipermeable membrane constitutes a space between the first inlet and the first outlet and a space between the second inlet and the second outlet, wherein the liquid-feeding pump and the liquid-returning pump are configured to perfuse the cell culture liquid from the first inlet-connected liquid feeding circuit to the first outlet-connected liquid feeding circuit through the culture liquid component controller, wherein the component controlling liquid pump is configured to perfuse the component controlling liquid from the second inlet-connected liquid feeding circuit to the second outlet-connected liquid feeding circuit through the culture liquid component controller, wherein the liquid-returning pump and the component controlling liquid pump are configured to feed the cell culture liquid in the cell culture vessel and the component controlling liquid in the component controlling liquid storage vessel to the culture liquid component controller, wherein the liquid-returning pump and the component controlling liquid pump are configured to return the cell culture liquid and the component controlling liquid, which was fed to the culture liquid component controller where unnecessary substances in the cell culture liquid are allowed to be in contact with useful substances in the component controlling liquid, and wherein feed amount V1 of liquid per hour by the liquid-feeding pump and return amount V2 of liquid per hour by the liquid-returning pump satisfy $0.9 \times V1 \leq V2 \leq 1.1 \times V1$, and the total amount of cell culture liquid containing the cells changes within the range of 10%.

17. The cell culture system according to claim 16, further comprising a filter which is disposed in the first inlet-connected liquid feeding circuit and is configured to pass the cell culture liquid and does not pass cells or cell aggregates at the inner end of the cell culture vessel.

18. The cell culture system according to claim 16, wherein the culture liquid component controller is formed of hollow fibers.

19. A method for culturing cells, comprising:
a) providing the cell culture system according to claim 16;
b) supplying cells and the cell culture liquid to the cell culture vessel and supplying the culture liquid component controlling liquid to the component controlling liquid storage vessel, and;
c) continuously perfusing the cell culture liquid and the component controlling liquid,
wherein feed amount V1 of liquid per hour by the liquid-feeding pump and return amount V2 of liquid per hour by the liquid-returning pump are controlled to satisfy $0.9 \times V1 \leq V2 \leq 1.1 \times V1$, and the total amount of cell culture liquid containing the cells is controlled to change within the range of 10%.

20. The cell culture system according to claim 16, wherein the cells are mammalian cells.

21. The cell culture system according to claim 20, wherein the mammalian cells are embryonic stem cells (ES cells), induced pluripotent stem cells (iPS cells), mesenchymal stem cells, hematopoietic stem cells and/or cells differentiated and induced from these cells.

22. The cell culture system according to claim 16, wherein the cells are cells applicable to floating culture, adhesive cells, cells forming cell aggregates and/or cells capable of adhering to a particle carrier.

23. The cell culture method according to claim 22, wherein the cells capable of adhering to a particle carrier are cultured by placing the cells and the particle carrier in a cell culture vessel.

24. A method for culturing cells, comprising:
placing at least cells and a cell culture liquid to a cell culture vessel to culture the cells;
feeding the cell culture liquid in the cell culture vessel by a liquid-feeding pump;
bringing the cell culture liquid and a component controlling liquid into contact with each other through a membrane to reduce a difference between concentrations of components of the cell culture liquid and concentrations of components of the component controlling liquid; and
returning the cell culture liquid brought into contact with the component controlling liquid through the membrane by a liquid-returning pump,
wherein feed amount V1 of liquid per hour in the feeding of the cell culture liquid and return amount V2 of liquid per hour in the returning of the cell culture liquid are controlled to satisfy $0.9 \times V1 \leq V2 \leq 1.1 \times V1$ by independently controlling the liquid-feeding pump and the liquid-returning pump, and
the total amount of cell culture liquid containing the cells changes within the range of 10%.

25. A method for culturing cells, comprising:
placing at least cells and a cell culture liquid to a cell culture vessel to culture the cells;
feeding a component controlling liquid in a component controlling liquid storage vessel by a component controlling liquid pump;
bringing the cell culture liquid and the component controlling liquid into contact with each other through a membrane to reduce a difference between concentrations of components of the cell culture liquid and concentrations of components of the component controlling liquid; and
returning the component controlling liquid brought into contact with the cell culture liquid through the membrane by the component controlling liquid pump,
wherein feed amount V1 of liquid per hour in the feeding of the component controlling liquid and return amount V2 of liquid per hour in the returning of the component controlling liquid are controlled to satisfy $0.9 \times V1 \leq V2 \leq 1.1 \times V1$ by controlling the component controlling liquid pump, and
the total amount of cell culture liquid containing the cells changes within the range of 10%.

26. A method for culturing cells, comprising:
placing at least cells and a cell culture liquid to a cell culture vessel to culture the cells;
feeding the cell culture liquid in the cell culture vessel by a liquid-feeding pump and a component controlling liquid in a component controlling liquid storage vessel by a component controlling liquid pump;
bringing the cell culture liquid and the component controlling liquid into contact with each other through a membrane to reduce a difference between concentrations of the components of the cell culture liquid and concentrations of the components of the component controlling liquid; and
returning the cell culture liquid and the component controlling liquid brought into contact with each other through the membrane by a liquid-returning pump and the component-controlling liquid-pump,
wherein feed amount V1 of liquid per hour in the feeding of the cell culture liquid and return amount V2 of liquid per hour in the returning of the cell culture liquid are controlled to satisfy $0.9 \times V1 \leq V2 \leq 1.1 \times V1$ by independently controlling the liquid-feeding pump and the liquid-returning pump, and the total amount of cell culture liquid containing the cells changes within the range of 10%.

* * * * *